US008282939B2

(12) United States Patent
Faber et al.

(10) Patent No.: US 8,282,939 B2
(45) Date of Patent: Oct. 9, 2012

(54) ATTENUATED LIVE TRIPLE G PROTEIN RECOMBINANT RABIES VIRUS VACCINE FOR PRE- AND POST-EXPOSURE PROPHYLAXIS OF RABIES

(75) Inventors: Milosz Faber, Lansdowne, PA (US); Bernhard Dietzschold, Newtown Square, PA (US); Douglas Craig Hooper, Medford, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 52 days.

(21) Appl. No.: 12/879,335

(22) Filed: Sep. 10, 2010

(65) Prior Publication Data

US 2011/0064764 A1 Mar. 17, 2011

Related U.S. Application Data

(60) Provisional application No. 61/241,439, filed on Sep. 11, 2009.

(51) Int. Cl.
*A61K 39/205* (2006.01)
*C12N 7/00* (2006.01)
*C12N 7/01* (2006.01)

(52) U.S. Cl. .............. 424/224.1; 435/235.1; 435/320.1; 424/199.1; 424/204.1

(58) Field of Classification Search ........................ None
See application file for complete search history.

(56) References Cited

U.S. PATENT DOCUMENTS

| | | | | |
|---|---|---|---|---|
| 7,074,413 | B2 | 7/2006 | Dietzschold et al. | 424/199.1 |
| 7,223,584 | B2 * | 5/2007 | Dietzschold et al. | 435/235.1 |
| 7,695,724 | B2 * | 4/2010 | Dietzschold et al. | 424/224.1 |
| 2008/0003657 | A1 * | 1/2008 | Dietzschold et al. | 435/235.1 |

OTHER PUBLICATIONS

NCBI Blast:Nucleotide Sequence (1575 letters) 4 pages, Dec. 17, 2011, SEQ 7 vs SEQ 5 from PGpub-pat'782.*

Dietzschold, et al., "In vitro growth and stability of recombinant rabies viruses designed for vaccination of wildlife", *Vaccine*, 23 (2004) 518-524.

Dietzschold, et al., "*Intervention of Rabies Through Pattern Recognition Receptor Signaling", International Conference on Rabies in the Americas XIX*, Centers for Disease Control and Prevention, Atlanta, GA, (Sep. 28, 2008), p. 57.

Faber, et al., "Overexpression of the Rabies Virus Glycoprotein Results in Enhancement of Apoptosis and Antiviral Immune Response", *Journal of Virology*, Apr. 2002, p. 3374-3381.

Faber, et al., "A Single Amino Acid Change in Rabies Virus Glycoprotein Increases Virus Spread and Enhances Virus Pathogenicity", *Journal of Virology*, Nov. 2005, p. 14141-14148.

Faber, et al., "Dominance of a Nonpathogenic Glycoprotein Gene over a Pathogenic Glycoprotein Gene in Rabies Virus", *Journal of Virology*, Jul. 2007, p. 7041-7047.

Faber, et al., Effective preexposure and postexposure prophylaxis of rabies with a highly attenuated recombinant rabies virus, *PNAS*, Jul. 6, 2009, vol. 106, No. 27, p. 11300-11305.

Hosokawa-Muto, et al., "Characterization of Recombinant Rabies Virus Carrying Double Glycoprotein Genes", *Microbiol. Immunol.*, 50(3), 187-196, 2006.

Li, et al., "Infection of monocytes or immature dendritic cells (DCs) with an attenuated rabies virus results in DC maturation and a strong activation of the NFkB signaling pathway", *Vaccine*, Jan. 17, 2008; 26(3): 419-426.

Morimoto, et al., "Pathogenicity of Different Rabies Virus Variants Inversely Correlates with Apoptosis and Rabies Virus Glycoprotein Expression in Infected Primary Neuron Cultures", *Journal of Virology*, Jan. 1999, p. 510-518.

* cited by examiner

*Primary Examiner* — Mary E Mosher
*Assistant Examiner* — Myron Hill
(74) *Attorney, Agent, or Firm* — Drinker Biddle & Reath LLP

(57) ABSTRACT

The invention provides a recombinant rabies viruses comprising three copies of a mutated G gene wherein each G gene encodes a rabies virus glycoprotein having the amino acid 194 mutated to a serine and the amino acid 333 is mutated to a glutamic acid. The recombinant rabies virus is nonpathogenic in immunodeficient mammals and can be used in a vaccine to induce an immune response protect mammals from infection by rabies virus as well as clear a pre-existing rabies virus infection from neural tissues.

9 Claims, 7 Drawing Sheets

SEQUENCE LISTING

```
<160> NUMBER OF SEQ ID NOS: 7

<210> SEQ ID NO 1
<211> LENGTH: 50
<212> TYPE: DNA
<213> ORGANISM: Artificial
<220> FEATURE:
<223> OTHER INFORMATION: Chemically synthesized primer designated as
      InterG BA(+)

<400> SEQUENCE: 1
cgatgtatac gtacgttttt gcgatcgccg tcctttcaac gatccaagtc              50

<210> SEQ ID NO 2
<211> LENGTH: 49
<212> TYPE: DNA
<213> ORGANISM: Artificial
<220> FEATURE:
<223> OTHER INFORMATION: Chemically synthesized primer designated as
      InterG AN(-)

<400> SEQUENCE: 2
cttagcgcta gcaaaaaggc gcgccggagg ggtgttagtt tttttcatg               49

<210> SEQ ID NO 3
<211> LENGTH: 42
<212> TYPE: DNA
<213> ORGANISM: Artificial
<220> FEATURE:
<223> OTHER INFORMATION: Chemically synthesized primer designated as
      SADB19 AscI(+)

<400> SEQUENCE: 3
cgaatttatt ggcgcgccaa gatggttcct caggctctcc tg                      42

<210> SEQ ID NO 4
<211> LENGTH: 42
<212> TYPE: DNA
<213> ORGANISM: Artificial
<220> FEATURE:
<223> OTHER INFORMATION: Chemically synthesized primer designated as
      SADB19 NheI(-)

<400> SEQUENCE: 4
cttatcagct agctagctag ttacagtctg gtctcacccc ca                      42

<210> SEQ ID NO 5
<211> LENGTH: 39
<212> TYPE: DNA
<213> ORGANISM: Artificial
<220> FEATURE:
<223> OTHER INFORMATION: Chemically synthesized primer designated as
      SADB19 BsiWI(+)

<400> SEQUENCE: 5
cgatgtatac gtacgaagat ggttcctcag gctctcctg                          39
```

```
<210> SEQ ID NO 6
<211> LENGTH: 42
<212> TYPE: DNA
<213> ORGANISM: Artificial
<220> FEATURE:
<223> OTHER INFORMATION: Chemically synthesized primer designated as
      SADB19 AsiSI(-)

<400> SEQUENCE: 6
gaatctagag cgatcgccgt ttacagtctg gtctcacccc ca                              42

<210> SEQ ID NO 7
<211> LENGTH: 1575
<212> TYPE: DNA
<213> ORGANISM: Rabies virus
<220> FEATURE:
<223> OTHER INFORMATION: Rabies virus glycoprotein DNA sequence with a
      mutation to encode a serine at position 194

<400> SEQUENCE: 7
atggttcctc aggctctcct gtttgtaccc cttctggttt ttccattgtg ttttgggaaa          60
ttccctattt acacgatacc agacaagctt ggtccctgga gtccgattga catacatcac         120
ctcagctgcc caaacaattt ggtagtggag gacgaaggat gcaccaacct gtcagggttc         180
tcctacatgg aacttaaagt tggatacatc ttagccataa agtgaacgg gttcacttgc          240 acaggcgttg tgacggaggc tgaaacctac actaacttcg ttggttatgt cacaaccacg         300
ttcaaaagaa agcatttccg cccaacacca gatgcatgta gagccgcgta caactggaag         360
atggccggtg accccagata tgaagagtct ctacacaatc cgtaccctga ctaccgctgg         420
cttcgaactg taaaaaccac caaggagtct ctcgttatca tatctccaag tgtggcagat         480
ttggacccat atgacagatc ccttcactcg agggtcttcc ctagcgggaa gtgctcagga         540
gtagcggtgt cttctaccta ctgctccact aaccacgatt acaccatttg atgcccgag          600 aatccgagac tagggatgtc ttgtgacatt tttacctcca gtagagggaa gagagcatcc         660
aaagggagtg agacttgcgg ctttgtagat gaaagaggcc tatataagtc tttaaaagga         720
gcatgcaaac tcaagttatg tggagttcta ggacttagac ttatggatgg aacatgggtc         780
tcgatgcaaa catcaaatga aaccaaatgg tgccctcccg ataagttggt gaacctgcac         840
gactttcgct cagacgaaat tgagcacctt gttgtagagg agttggtcag gaagagagag         900
gagtgtctgg atgcactaga gtccatcatg acaccaagt cagtgagttt cagacgtctc         960
agtcatttaa gaaaacttgt ccctgggttt ggaaaagcat ataccatatt caacaagacc        1020
ttgatggaag ccgatgctca ctacaagtca gtcgagactt ggaatgagat cctcccttca        1080
aaagggtgtt taagagttgg ggggaggtgt catcctcatg tgaacggggt gttttcaat         1140 ggtataatat taggacctga cggcaatgtc ttaatcccag agatgcaatc atccctcctc        1200
cagcaacata tggagttgtt ggaatcctcg gttatccccc ttgtgcaccc cctggcagac        1260
ccgtctaccg tttcaagga cggtgacgag gctgaggatt tgttgaagt tcaccttccc         1320 gatgtgcaca atcaggtctc aggagttgac ttgggtctcc cgaactgggg aagtatgta         1380 ttactgagtg caggggccct gactgccttg atgttgataa ttttcctgat gacatgttgt        1440
agaagagtca atcgatcaga acctacgcaa cacaatctca gagggacagg gagggaggtg        1500
tcagtcactc cccaaagcgg gaagatcata tcttcatggg aatcacacaa gagtgggggt        1560
gagaccagac tgtaa                                                        1575
```

ATTENUATED LIVE TRIPLE G PROTEIN RECOMBINANT RABIES VIRUS VACCINE FOR PRE- AND POST-EXPOSURE PROPHYLAXIS OF RABIES

CROSS-REFERENCE TO RELATED APPLICATION

This application claims the benefit of U.S. Provisional Application No. 61/241,439, filed Sep. 11, 2009, the entire disclosure of which is incorporated herein by reference.

REFERENCE TO GOVERNMENT GRANT

This invention was supported in part by grant numbers R01 AI060686, AI060005 and AI077033 from the National Institutes of Health. The U.S. Government has certain rights in this invention.

FIELD OF THE INVENTION

The invention relates to nonpathogenic recombinant rabies virus comprising multiple copies of a modified external surface glycoprotein (G) gene. The recombinant rabies virus can be used as a vaccine to protect against infection from rabies virus and to clear rabies virus from nervous tissues after an infection has occurred.

BACKGROUND OF THE INVENTION

Rabies causes an estimated 55,000 human deaths globally each year, 23,750 of which occur in Africa (Knobel et al., 2005, *Bull World Health Organ* 83:360-368). Moreover, 11 million people undergo rabies postexposure prophylaxis (PEP) worldwide each year. Rabies is a zoonotic disease with dogs remaining the principal host in Asia, parts of America, and large parts of Africa, and rabid dogs are the cause of most human rabies cases (Hampson et al., 2009, *PLoS Biol* 7:e53). It is believed that between 30% to 60% of the victims of dog bites are children under the age of 15. Inappropriate dog vaccination programs, limited access to vaccination, and postexposure treatment of individuals that have been exposed to rabid dogs are major problems in developing countries.

Rabies virus (RV), a negative-stranded RNA virus of the rhabdoviridae family, has a relatively simple, modular genome that encodes 5 structural proteins: a RNA-dependent RNA polymerase (L), a nucleoprotein (N), a phosphorylated protein (P), a matrix protein (M), and an external surface glycoprotein (G). The N, P, and L together with the genomic RNA form the ribonucleoprotein complex (RNP). The main feature of rabies virus is neuroinvasiveness, which refers to its unique ability to invade the central nervous system (CNS) from peripheral sites. Virus uptake, axonal transport, trans-synaptic spread, and the rate of viral replication are key factors that determine the neuroinvasiveness of a RV (Dietzschold et al., 1983, *Proc Natl Acad Sci USA* 80:70-74; Dietzschold et al., 1987, *Proc Natl Acad Sci USA* 84:9165-9169; Morimoto et al., 2000, *J Neurovirol* 6:373-381; Morimoto, et al., 1999, *J Virol* 73:510-518). The regulation of viral replication also appears to be one of the important mechanisms contributing to RV pathogenesis. Pathogenic RV strains replicate at a lower rate than attenuated strains, which helps preserve the structure of neurons that is used by the viruses to reach the CNS. In addition, the lower expression levels of viral antigens, in particular the RV G, which is the major viral antigen responsible for the induction of protective immunity, hinders early detection by the host immune system (Morimoto, et al., 1999, *J Virol* 73:510-518). In contrast to wildlife RVs, most attenuated RV strains replicate very quickly and express large amounts of G, thereby inducing strong adaptive immune responses that result in virus clearance. These properties provide the basis for the use of attenuated RV strains for the pre- and PEP of rabies. A live-attenuated RV vaccine is likely to provide effective immunization with a single dose, which has practical, cost, and logistical advantages over conventional multi-dose vaccines with respect to the worldwide eradication of dog rabies. In addition, because live-attenuated RV vaccines are capable of inducing immune responses that can clear virulent RVs from the CNS (Phares et al., 2006, J Immunol 176:7666-7675; Roy et al., 2008, J Neurovirol 14:401-411), there is the possibility that such vaccines could serve as the foundation for the treatment of early stage human rabies.

Apart from efficacy, the most important prerequisite for the use of live-attenuated RV vaccines in both preexposure and postexposure immunization against rabies is safety. In this respect, the availability of reverse genetics technology, which allows the modification of viral elements that account for pathogenicity and immunogenicity, has made the systematic development of safer and more potent modified-live rabies vaccine feasible. For example, the pathogenicity of fixed RV strains (i.e., ERA, SAD) can be completely abolished for immunocompetent mice by introducing single amino acid exchanges in their G (Faber et al., 2005, *J Virol* 79:14141-14148), and RVs containing a SADB19 G with an $Arg_{333} \rightarrow Glu_{333}$ mutation are nonpathogenic for adult mice after intracranial/intracerebral (i.c.) inoculation, and that an $Asn_{194} \rightarrow Ser_{194}$ mutation in the same gene prevents the reversion to pathogenic phenotype (Faber et al., 2005, *J Virol* 79:14141-14148; Dietzschold et al., 2004, *Vaccine* 23:518-524). The G containing both mutations has been designated as GAS. Using the GAS gene, the single and double GAS RV variants, SPBNGAS and SPBNGAS-GAS, respectively, were constructed (Faber et al., 2005, *J Virol* 79:14141-14148; Li et al., 2008, *Vaccine* 26:419-426). The introduction of a second G gene significantly improves the efficacy of the vaccine by enhancing its immunogenicity through higher expression of G (Faber et al., 2002, *J Virol* 76:3374-3381). Elevated G expression is associated with the strong up-regulation of genes related to the NFκB signaling pathway, including IFN-α/β and IFN-γ (Li et al., 2008, *Vaccine* 26:419-426) and increased cell death (Faber et al., 2002, *J Virol* 76:3374-3381). Furthermore, the presence of two G genes also decreases substantially the probability of reversion to pathogenicity because the nonpathogenic phenotype determined by GAS is dominant over a pathogenic G that could emerge during virus growth in vivo or in vitro (Faber et al., 2007, *J Virol* 81:7041-7047).

Controlling rabies virus infection in domestic and wildlife animals, therefore, not only reduces the mortality in these animals but also reduces the risks of human exposure. Pre-exposure vaccinations for people who are constantly at risk further prevent human rabies, as do post-exposure immunizations for people who are bitten by rabid or suspected rabid animals. A recombinant vaccinia virus expressing rabies virus glycoprotein (VRG) has been used to control rabies in wildlife. Inactivated rabies virus vaccines are used to immunize domestic animals, particularly pets. Purified and inactivated rabies virus vaccines are used for humans in the pre- or post-exposure settings. Although these vaccines are effective, annual vaccinations are required to maintain adequate immunity in pets. For humans, multiple doses of the inactivated tissue culture vaccines are required to stimulate optimal immune responses. Furthermore, current tissue culture vaccines are expensive; thus most people in need of vaccinations (in developing countries) cannot afford them. Hence, there is a need to develop more efficacious and affordable rabies virus vaccines.

SUMMARY OF THE INVENTION

The invention provides a nonpathogenic recombinant rabies virus comprising at least three copies of a mutated G gene. The mutated G gene encodes a rabies virus glycoprotein wherein the amino acid 194 is serine and the amino acid 333 is glutamic acid in the glycoprotein.

In one embodiment, the mutated G gene is encoded by SEQ ID NO:7.

In another embodiment, the recombinant rabies virus further comprises a foreign antigen. In some instances, the antigen is derived from a human. In other instances, the antigen is derived from an animal pathogen.

In one embodiment, the recombinant rabies virus further expresses a gene encoding an immune-stimulatory protein.

The invention provides a vaccine comprising a nonpathogenic recombinant rabies virus comprising at least three copies of a mutated G gene, wherein said mutated G gene encodes a rabies virus glycoprotein wherein the amino acid 194 is serine and the amino acid 333 is glutamic acid in the glycoprotein.

The invention also provides a pharmaceutical composition comprising a nonpathogenic recombinant rabies virus comprising at least three copies of a mutated G gene, wherein said mutated G gene encodes a rabies virus glycoprotein wherein the amino acid 194 is serine and the amino acid 333 is glutamic acid in the glycoprotein, and a pharmaceutically acceptable carrier.

The invention also provides a method of inducing an immune response to rabies virus in a mammal. The method comprises administering to a mammal an effective amount of a nonpathogenic recombinant rabies virus comprising at least three copies of a mutated G gene, wherein the mutated G gene encodes a rabies virus glycoprotein wherein the amino acid 194 is serine and the amino acid 333 is glutamic acid in the glycoprotein.

The invention also provides a method of protecting a mammal from rabies virus. The method comprises administering to a mammal an effective amount of a nonpathogenic recombinant rabies virus comprising at least three copies of a mutated G gene, wherein the mutated G gene encodes a rabies virus glycoprotein wherein the amino acid 194 is serine and the amino acid 333 is glutamic acid in the glycoprotein.

ABBREVIATIONS AND SHORT FORMS

The following abbreviations and short forms are used in this specification.

"BBB" means blood brain barrier.
"CNS" means central nervous system.
"FFU" means focus-forming units.
"GAS" means an RV G containing both an $Arg_{333} \rightarrow Glu_{333}$ mutation and an $Asn_{194} \rightarrow Ser_{194}$.
"i.c." means intracerebral or intracranial.
"i.m." means intramuscular.
"MOI" means multiplicity of infection.
"NA" means neuroblastoma.
"PEP" means postexposure prophylaxis.
"TCIU" means tissue culture infective units.
"VNA" means virus-neutralization antibody.
"RV" means rabies virus.

"L" means RNA-dependent RNA polymerase in the context of RV.
"N" means nucleoprotein in the context of RV.
"P" means phosphorylated protein in the context of RV.
"M" means matrix protein in the context of RV.
"G" means external surface glycoprotein in the context of RV.
"RNP" means ribonucleoprotein complex.

DEFINITIONS

The definitions used in this application are for illustrative purposes and do not limit the scope of the invention.

The articles "a" and "an" are used herein to refer to one or to more than one (e.g., to at least one) of the grammatical object of the article. By way of example, "an element" means one element or more than one element.

The term "animal" has its ordinary meaning, and is meant to include human beings.

As used herein, each "amino acid" is represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty L-amino acids commonly found in naturally occurring peptides. "Nonstandard amino acid residues" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change a peptide's circulating half life without adversely affecting activity of the peptide. Additionally, a disulfide linkage may be present or absent in the peptides of the invention.

"Attenuated" as used herein in the context of a live virus, such as a rabies virus, means that the ability for the virus to infect a cell or subject and/or its ability to produce disease is reduced (for example, eliminated). Typically, an attenuated virus retains at least some capacity to elicit an immune response following administration to an immunocompetent subject. In some cases, an attenuated virus is capable of eliciting a protective immune response without causing any signs or symptoms of infection.

As used herein, the term "gene" refers to an element or combination of elements that are capable of being expressed in a cell, either alone or in combination with other elements. In general, a gene comprises (from the 5' to the 3' end): (1) a promoter region, which includes a 5' nontranslated leader sequence capable of functioning in any cell such as a prokaryotic cell, a virus, or a eukaryotic cell (including transgenic animals); (2) a structural gene or polynucleotide sequence, which codes for the desired protein; and (3) a 3' nontranslated region, which typically causes the termination of transcription and the polyadenylation of the 3' region of the RNA sequence. Each of these elements is operably linked by sequential attachment to the adjacent element.

As used herein, "gene products" include any product that is produced in the course of the transcription, reverse-transcription, polymerization, translation, post-translation and/or expression of a gene. Gene products include, but are not limited to, proteins, polypeptides, peptides, peptide fragments, or polynucleotide molecules.

"Homologous" as used herein, refers to the subunit sequence similarity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. By way of example, the DNA sequences 3'ATTGCC5' and 5'TATGGC3' are 50% homologous.

As used herein, "homology" is used synonymously with "identity."

"Isolated" means altered or removed from the natural state through the actions of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant," as used herein, refers to either a nucleic acid or protein comprising a mutation.

A "nucleic acid" refers to a polynucleotide and includes poly-ribonucleotides and poly-deoxyribonucleotides.

The term "oligonucleotide" typically refers to short polynucleotides of about 50 nucleotides or less in length. It will be understood that when a nucleotide sequence is represented herein by a DNA sequence (e.g., A, T, G, and C), this also includes the corresponding RNA sequence (e.g., a, u, g, c) in which "u" replaces "T".

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids which can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptide, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "polynucleotide" includes cDNA, RNA, DNA/RNA hybrid, anti-sense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the invention are alterations of a wild type or synthetic gene, including but not limited to deletion, insertion, substitution of one or more nucleotides, or fusion to other polynucleotide sequences, provided that such changes in the primary sequence of the gene do not alter the expressed peptide ability to elicit passive immunity.

"Pharmaceutically acceptable" means physiologically tolerable, for either human or veterinary applications.

As used herein, "pharmaceutical compositions" include formulations for human and veterinary use.

As used herein, "promoter" refers to a region of a DNA sequence active in the initiation and regulation of the expression of a structural gene. This sequence of DNA, usually upstream to the coding sequence of a structural gene, controls the expression of the coding region by providing the recognition for RNA polymerase and/or other elements required for transcription to start at the correct site.

A "sample," as used herein, refers to a biological sample from a subject, including normal tissue samples, blood, saliva, feces, or urine. A sample can also be any other source of material obtained from a subject which contains a compound or cells of interest.

The phrase "sufficient to protect an animal from infection" is used herein to mean an amount sufficient to prevent, and preferably reduce by at least about 30 percent, more preferably by at least 50 percent, more preferably by at least 90 percent, most preferably at least 99 percent, a clinically significant change in at least one feature of pathology normally caused by the disease.

The term "vaccine" as used herein is defined as a material used to provoke an immune response after administration of the material to a mammal.

A "vector," as used herein, refers to a replicon, such as plasmid, phage or cosmid, to which another DNA segment may be attached so as to bring about the replication of the attached segment.

The term "virus" as used herein is defined as a particle consisting of nucleic acid (RNA or DNA) enclosed in a protein coat, with or without an outer lipid envelope, which is capable of replicating within a whole cell.

DESCRIPTION OF THE FIGURES

It is to be understood that the following detailed description is exemplary and explanatory only, and are not restrictive of the material methods, devices, and kits. The accompanying drawings, which are incorporated herein by reference, and which constitute a part of this specification, illustrate certain embodiments, and together with the detailed description, and serve to explain the principles of the materials and methods. The drawings are exemplary only, and should not be construed as limiting the materials, methods, and compositions described herein.

FIGS. 2B and 2C are charts depicting replication of viral genomic RNA (FIG. 2B) and transcription of viral mRNA (FIG. 2C) in NA cells infected with SPBAANGAS-GAS-GAS or SPBAANGAS-GAS(−)-GAS(−).

FIGS. 3A through 3C, is a set of plots demonstrating survivorship in mice infected i.c. at day 1, day 5, and day 10 after birth with different recombinant RVs. Litters of 1-(FIG. 3A), 5-(FIG. 3B), and 10-(FIG. 3C) day-old Swiss-Webster mice were infected i.c. with $10^3$ tissue culture infective units (TCIU) of SPBNGAS, SPBNGAS-GAS, SPBAANGAS-GAS-GAS or SPBAAN-GAS-GAS(−)-GAS (−). The mice were observed for 4 weeks for occurrence of clinical signs of rabies, and mortality rates were recorded daily. Three weeks after infection, blood samples were obtained from the surviving mice, and viral neutralizing antibody (VNA) titers were determined by using the rapid fluorescence inhibition test.

FIGS. 4A and 4B, is a series of plots depicting preexposure immunization of SPBAANGAS-GAS-GAS, SPBAANGAS-GAS(−)-GAS(−) and UV-inactivated SPBAANGAS-GAS-GAS in Swiss-Webster mice. Groups of 10 mice were injected i.m. with 100 μL of serial 10-fold dilutions (vaccine doses: $10^2$ to $10^5$ TCIU) of the recombinant RVs. Three weeks after immunization, mice were infected i.c. with 100 LD50 of DOG4 RV and observed for 4 weeks. FIG. 4A shows the percentage of survivors in the different immunization groups at 4 weeks after virus challenge. FIG. 4B shows the $ED_{50}$ values calculated from the survivorship rates in the 3 vaccination groups.

FIGS. 5A through 5C, is a series of plots demonstrating induction of blood brain barrier (BBB) permeability after i.c. infection with SPBAANGAS-GAS-GAS. 129/SvEv mice were injected with $10^7$ focus-forming units (FFU) of SPBAANGAS-GAS-GAS into the right hemisphere. BBB permeability to the fluid phase marker sodium fluorescein (Na-fluorescein) was assessed 6 and 8 days later in the right and left cortex and in cerebellum. Levels of mRNAs specific for the T cell marker CD4 and the B cell marker CD19 in the same tissues were assessed by quantitative RT-PCR. BBB permeability is expressed as the amount of Na-fluorescein detected in infected CNS tissues normalized to the amount in uninfected CNS tissue (FIG. 5A). CD4 (FIG. 5B) and CD19 (FIG. 5C) mRNA levels are expressed as the fold increase in infected over the levels detected in uninfected brain tissue. Significance of differences between the signals in normal and infected tissues were assessed by the Mann-Whitney test. *, $P<0.05$; **, $P<0.01$.

FIGS. 6A and 6B, is a series of plots depicting postexposure treatment with SPBNAAGAS-GAS-GAS of mice after infection with DOG RV. Groups of 10 adult Swiss-Webster mice infected i.m. with 10 IM-$LD_{50}$ of DOG4 RV and treated i.c (FIG. 6A) or i.m. (FIG. 6B) at different times p.i. with SPBAANGAS-GAS-GAS.

DETAILED DESCRIPTION OF THE INVENTION

Figure 1:
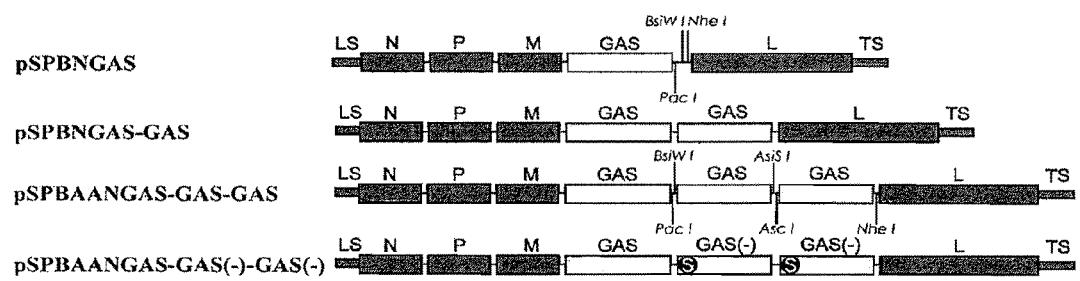
FIG. 1 is a schematic of the construction of recombinant RVs containing 1, 2, or 3 modified G genes. To abolish the pathogenicity, two amino acid substitutions were introduced into RV G ($Arg_{333} \rightarrow Glu_{333}$ and $Asn_{194} \rightarrow Ser_{194}$) resulting in GAS. In SPBAANGAS-GAS(−)-GAS(−), all ATG codons of the last two GAS genes were scrambled. LS=leader sequence; N=nucleoprotein; M=matrix protein; G=glycoprotein; L=RNA-dependent RNA polymerase; TS=terminal sequence; S=scrambled ATG codons.

The present invention relates to effective and affordable virus vaccines for humans as well as for animals, to methods of making the same, and to methods of using the same for inducing an immune response, preferably a protective immune response in animals and humans. Suitable viruses include, but are not limited to, rabies virus (RV).

In one embodiment, invention relates to a recombinant nonpathogenic, live rabies virus that has been modified to be nonpathogenic and eliminate revision of the virus to a pathogenic form. For example, the pathogenicity of RV strains can be completely abolished for immunocompetent mice by introducing single amino acid exchanges in their G gene. RVs containing a G having a mutation of $Arg_{333} \rightarrow Glu_{333}$ are nonpathogenic for adult mice after intracranial/intracerebral (i.c.) inoculation, and a mutation of $Asn_{194} \rightarrow Ser_{194}$ mutation in the same gene prevents the reversion to pathogenic phenotype. The G gene containing both mutations is designated as GAS. GAS has been described in U.S. application Ser. No. 11/571, 842, now U.S. Pat. No. 7,695,724, which is incorporated herein by reference in its entirety.

The present invention is an improvement to attenuated rabies viruses in the art including variants expressing two GAS genes, in that the RV variants of the invention comprising at least three copies of GAS are nonpathogenic when inoculated into, for example, 5 day-old suckling mice, thereby demonstrating that the RV variants do not exhibit residual pathogenicity. The RV variants of the invention are in improvement to existing attenuated RV because the RV variants comprising at least three copies of GAS are nonpathogenic in immunodeficient mammals. The present invention has solved the problem in the art of associated with residual pathogenicity by generating RV variants, which have a reduced or otherwise eliminated pathogenicity in suckling mice and immmunodeficient mammals.

Although RV variants containing one or two GAS genes have been shown to be very safe for normal animals, these variants are pathogenic for immunodeficient animals. The present invention relates to the unexpected observation that an RV variant that contains three copies of the GAS gene possesses unique attributes including the lack of pathogenicity and immunogenicity for very young mice and the capacity to prevent lethal rabies encephalomyelitis even when administered after CNS infection with a highly pathogenic RV strain. The lack of pathogenicity together with excellent immunogenicity and the capacity to deliver immune effectors to CNS tissues makes an RV variant comprising three copies of the GAS gene a therapeutic vaccine for preexposure and postexposure prophylaxis of rabies. The capacity to raise a protective response in neonatal mice indicated that the triple GAS vaccine is safe and effective for young dogs and present little risk for young children who may be exposed to rabies virus.

Any strain of rabies virus can be used in the generation of RV variants comprising three GAS genes. For example, the RV variants of the invention can be derived from the SAD Bern strain or the SAD B19 strain.

Also included in the invention are host cells for producing the mutant virus, as well as a method of producing the same. Preferably, the host cell is a mammalian host cell, preferably a BHK cell, and more preferably, BSR (a BHK-21 clone).

The RV variant of the invention can be used as a vaccine. In some instance, the vaccine compositions of the invention may contain an adjuvant. The vaccine may be prepared using any pharmaceutically acceptable carrier or vehicle, including Hanks basic salt solution (HBSS) or phosphate buffered saline (PBS). The vaccine compositions can be administered by any known route, including intradermal, intracranial/intracerebral, intramuscular and subcutaneous, which are preferred, as well as oral, via skin (epidermal abrasion) or intranasal.

In one embodiment of the present invention, the RV variant comprising at least three copies of GAS encodes a protein having immunoprotective activity against live rabies virus. In still another embodiment of the present invention, the RV variant provides 100% immunoprotection against rabies virus. In still another embodiment of the present invention, the RV variant controls rabies in humans, pets and wild life.

In yet another embodiment of the present invention the RV variant expressing at least three copies of GAS is able to induce immune mechanisms capable of clearing a pre-existing infection with wild-life RV from nervous tissues including the central nervous system.

The invention further provides embodiments of a nonpathogenic recombinant rabies virus comprising a foreign gene expressing a protein antigen. For example, the foreign gene is not derived from rabies virus genome. The protein antigen may comprise at least one antigen from a pathogen. An embodiment provides a vaccine comprising a recombinant rabies virus comprising a foreign gene expressing a protein antigen and a pharmaceutically acceptable carrier.

Composition

Embodiments of the present invention provide recombinant nonpathogenic, live rabies viruses that have been modified to be nonpathogenic and eliminate revision of the virus to a pathogenic form. The amino acid(s) in the G protein of a live rabies virus that result in a pathogenic form of the virus can be determined and the G gene, or more specifically the codon(s) for the one or more amino acids in the G gene, can be modified by exchange of one or more nucleotides. The modified G gene provides for a nonpathogenic live rabies virus that eliminates or resists subsequent mutation resulting in a change of amino acids in the expressed glycoprotein from occurring.

One approach to obtaining more potent and safer RV vaccines is through the use of reverse genetics technology to develop recombinant RVs. To increase the safety and immunogenicity of RV vaccines, distinct genetic alterations that affect the pathogenicity, but not the immunogenicity, of the virus can be introduced into the viral genome. For example, the recombinant RV can be engineered to carry a G gene in which $Arg_{333}$ is replaced with $Glu_{333}$ and in which $Asn_{194}$ is replaced with $Ser_{194}$. The G gene having both the $Glu_{333}$ and $Ser_{194}$ mutations is referred to as GAS (SEQ ID NO:7).

A recombinant virus expressing one copy of the GAS gene is termed SPBNGAS. A recombinant virus expressing two copies of the GAS gene is termed SPBNGAS-GAS. A recombinant virus expressing three copies of the GAS gene is termed SPBNGAS-GAS-GAS.

A recombinant RV comprising at least three copies of GAS is nonpathogenic and reversion to pathogenic phenotype is inhibited. In some instances, the RV comprising at least three copies of GAS is nonpathogenic in young mice, yet exhibits desirable immunogenicity. In other instances, the RV comprising at least three copies of GAS is nonpathogenic in immunodeficient mammals, yet exhibits desirable immunogenicity.

The present invention has solved the problem in the art associated with live-attenuated RV vaccines having residual pathogenicity. The present invention is based on the surprising finding that when a recombinant RV expresses three copies of GAS, a dramatic reduction in pathogenicity for suckling mice was observed. This unexpected finding has a profound advantage in developing more safe live attenuated rabies vaccines.

It was found that recombinant RV variants expressing at least three copies of GAS are not pathogenic or much less pathogenic for 5 day-old suckling mice as opposed to RV variants expressing one or two copies of GAS. Equally surprising is the capacity of vaccination with the RV to clear a pre-existing infection with wildlife RV that would otherwise be lethal. The introduction of the three copies of GAS into RV genome did not affect the growth rate of the virus in host cells and the final titer was similar to the parental strain. Furthermore, the introduced three copies of GAS did not affect the immunogenicity of the recombinant rabies viruses after administration into the subject. Desirable levels of rabies-specific antibody titers were detected in the subjects vaccinated with recombinant viruses possessing at least three copies of GAS. This makes the recombinant RV variants of the invention the safest live anti-rabies vaccines currently available.

RV comprising at least three copies of GAS are further attenuated than currently available attenuated rabies viruses. That is, currently available attenuated rabies viruses still induce rabies in neonatal animals. The present invention is an improvement to existing attenuated rabies viruses because an RV comprising at least three copies of GAS are not pathogenic in immunodeficient mice. The RV variants of the invention do not induce diseases in experimental immunodeficient mice or mice at very young age by any route of inoculation. However, the RV variants remain immunogenic and therefore can be developed into modified live rabies vaccines for humans and animals.

The pathogenicity of recombinant RVs containing modified G genes can be determine by injection of the recombinant virus into groups of adult Swiss Webster mice intracranially/intracerebrially with about $10^5$ infectious virus particles. After infection with the modified recombinant virus, clinical signs, body weight, and mortality rates can be monitored daily for several weeks or months to determine the pathogenicity of the modified viruses.

Recombinant RVs that contain three copies of GAS are considerably safer as compared to previously developed recombinant RVs. RVs containing three copies of GAS possess unique attributes including the lack of pathogenicity for very young mice and the capacity to prevent lethal rabies encephalomyelitis even when administered after CNS infection with a highly pathogenic RV strain. The unique attributes associated with having three copes of GAS allows for the use of the vaccine for both the preexposure and postexposure prophylaxis of rabies.

In accordance with the present invention there may be employed conventional molecular biology, microbiology, immunology, and recombinant DNA techniques within the skill of the art to generate the RV variants of the invention. Such techniques are explained fully in the literature. See, e.g., Sambrook et al, "Molecular Cloning: A Laboratory Manual" ($3^{rd}$ edition, 2001).

The nucleic acids of the present invention comprising at least three copies of GAS may be replicated in wide variety of cloning vectors in a wide variety of host cells.

In brief summary, the expression of nucleic acids encoding three copies of GAS is typically achieved by incorporating the construct into a rabies virus expression vector. This vectors is suitable for replication in eukaryotes.

Following the generation of the RV variants comprising at least three copies of GAS or portions thereof of the present invention, the RV variants can be used in a wide range of experimental and/or therapeutic purposes.

Methods

Clinically, the first symptoms of rabies in people may be nonspecific flu-like signs, such as malaise, fever, or headache. There may be discomfort or paresthesia at the site of exposure (bite), progressing within days to symptoms of cerebral dysfunction, anxiety, confusion, agitation, progressing to delirium, abnormal behavior, hallucinations, and insomnia.

Cellular pathology of rabies infection is defined by encephalitis and myelitis, including perivascular infiltration with lymphocytes, polymorphonuclear leukocytes, and plasma cells throughout the entire CNS. There may be cytoplasmic eosinophilic inclusion bodies (Negri bodies) in neuronal cells, including pyramidal cells of the hippocampus and Purkinje cells of the cerebellum, and within neurons of the cortex and other regions of the CNS, including the spinal ganglia.

The invention provides methods of producing a live rabies virus (for example, for use in an immunogenic composition, such as a vaccine) by introducing the vector system into a host cell. After transfection of vector system into a suitable host cell, live and optionally attenuated virus is recovered. Production and administration of a live rabies vaccine produced by such methods is also contemplated herein.

Also provided is a method of vaccinating a subject against rabies, which method comprises administering an effective amount of the live rabies vaccine according to the provided description to a subject, such that cells of the subject are infected with the rabies vaccine, wherein an anti-rabies immune response is produced in the subject. In one embodiment, the subject is a human. In another embodiment, the subject is a non-human animal. For instance, the non-human animal in some instances is a cat, dog, rat, mouse, bat, fox, raccoon, squirrel, opossum, coyote, or wolf.

One use of recombinant RVs such as SPBNGAS-GAS-GAS is for the vaccination of animals, and in particular human. The efficacy and safety of the of recombinant RVs such as SPBNGAS-GAS-GAS in vaccines can be first studied in laboratory mice and then in target larger animals.

In addition, the recombinant RVs of the invention can be further engineered to express foreign protein antigens and therefore have a utility as safe and effective vaccine vectors that can be used for vaccination against many antigens, including but not limited to tumor-associated antigens and microbial antigens.

In the context of the present invention, “tumor antigen” or “hyperporoliferative disorder antigen” or “antigen associated with a hyperproliferative disorder” refer to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin’s lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

In one embodiment, the tumor antigen of the present invention comprises one or more antigenic cancer epitopes immunologically recognized by tumor infiltrating lymphocytes (TIL) derived from a cancer tumor of a mammal.

Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD 19, CD20, idiotype) have been used as targets for passive immunotherapy with monoclonal antibodies with limited success.

The tumor antigen and the antigenic cancer epitopes thereof may be purified and isolated from natural sources such as from primary clinical isolates, cell lines and the like. The cancer peptides and their antigenic epitopes may also be obtained by chemical synthesis or by recombinant DNA techniques known in the arts Microbial antigens may be viral, bacterial, or fungal in origin. Examples of infectious virus include: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviruses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Poxviridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Examples of infectious bacteria include: *Helicobacter pyloris, Borelia burgdorferi, Legionella pneumophilia, Mycobacteria* sps (e.g. *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Entero-*

*coccus* sp., *Haemophilus influenzae, Bacillus anthracis, corynebacterium diphtheriae, corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema Treponema pertenue, Leptospira,* and *Actinomyces israelli*.

Examples of infectious fungi include: *Cryptococcus neoformans, Histoplasma capsulatum, Coccidioides immitis, Blastomyces dermatitidis, Chlamydia trachomatis, Candida albicans*. Other infectious organisms (i.e., protists) including: *Plasmodium falciparum* and *Toxoplasma gondii*.

The recombinant RV variant of the invention can further comprise an immunostimulatory agent. For example, the RV variant can be engineered to express a gene encoding an immune-stimulatory protein Administration of the live attenuated viruses disclosed herein may be carried out by any suitable means, including intracranial/intracerebral, parenteral injection (such as intraperitoneal, subcutaneous, or intramuscular injection), orally and by topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the virus as an aerosol suspension, and then causing the subject to inhale the respirable particles. Methods and apparatus for administering respirable particles of pharmaceutical formulations are well known, and any conventional technique can be employed. As a result of the vaccination the host becomes at least partially or completely immune to a rabies virus infection.

The vaccine composition containing the attenuated rabies virus in embodiments of the present invention can be administered to an animal susceptible to or otherwise at risk of rabies infection to enhance the individual animal's own immune response capabilities. Such an amount is an immunogenically effective dose. The virus may be live or killed. In this use, the precise amount again depends on the subject's state of health and weight, the mode of administration, the nature of the formulation, etc. Preferably the amount of attenuated or nonpathogenic live rabies virus in order to achieve sufficient immunoprotection (an immunogenically effective dose) should be an amount that the vaccine virus should be able to replicate sufficiently in the recipient so that enough viral antigen is presented to the immune system. Methods useful for characterizing effective amounts of nonpathogenic virus in a vaccine as well as rabies viruses which may be modified are disclosed by Dietzschold et. al. in PCT Application WO 01/70932 the contents of which are incorporated herein by reference in their entirety. Other methods and materials useful in the practice of embodiments of the present invention can include those described in U.S. Pat. Application Pub. No. 2002/0131981 the contents of which are incorporated herein by reference in their entirety. The amount of recombinant virus can be about $10^4$ FFU/ml or greater, preferably $10^6$ FFU/ml or greater. For use in baits, the amount of live recombinant virus is preferably greater than $10^6$ FFU/ml, more preferably $10^8$ FFU/ml or greater. The vaccine formulations preferably provide a quantity of attenuated rabies virus of the invention sufficient to effectively protect the subject against serious or life-threatening rabies virus infection.

The nonpathogenic rhabdovirus including a modified G gene that resists mutation to a pathogenic form of the virus may be live or killed. Sufficiently high doses of a single, nonpathogenic live recombinant rabies virus of the present invention can be administered to an animal providing protection against infection by all of the street rabies virus strains that are associated with different mammalian species in a diverse geographical location.

Methods and compositions of the present invention can confer clinical benefits to the treated mammals, providing clinically relevant titers against RV as measured for example by serum neutralization of RV followed by infection of mouse neuroblastoma cells and detection of infected cells with direct immunofluorescence antibody technique.

RV activity can be stabilized by the addition of excipients or by lyophilization. Stabilizers may include carbohydrates, amino acids, fatty acids, and surfactants and are known to those skilled in the art. Stabilizers may be used to improve the thermal stability of the recombinant viruses, especially for temperatures at or above about 37° C.

Live or killed viruses of the present invention may be administered topically, orally, i.c. or i.m. or locally or systemically. Oral administration using vaccines with bait can be used for treating wild or stray animals. The attenuated or nonpathogenic live rabies viruses, singularly or in combination, can be mixed with an appropriate pharmaceutical carrier prior to administration. Examples of generally used pharmaceutical carriers and additives are conventional diluents, binders, lubricants, coloring agents, disintegrating agents, buffer agents, isotonizing agents, preservants, anesthetics and the like. Pharmaceutical carriers that may be used are dextran, sucrose, lactose, maltose, xylose, trehalose, mannitol, xylitol, sorbitol, inositol, serum albumin, gelatin, creatinine, polyethylene glycol, non-ionic surfactants (e.g. polyoxyethylene sorbitan fatty acid esters, polyoxyethylene hardened castor oil, sucrose fatty acid esters, polyoxyethylene polyoxypropylene glycol) and similar compounds.

Pharmaceutical carriers may also be used in combination, such as polyethylene glycol and/or sucrose, polyoxyethylene sorbitan fatty acid esters, or polyoxyethylene sorbitan monooleate.

The suitability of recombinant rabies vaccines depends, in part, on the preservation of virus infectivity even after extended exposure to a wide range of temperatures. To determine if the addition of a third or more copy of the RV G gene, or modification of a G gene codon impairs the stability of the recombinant RVs, the viral titers of the recombinant viruses can be determined after different times of exposure to different temperatures. To obtain information on vaccine stability in a short period of time, the tests can be performed in absence of added virus stabilizers. Alternatively the stability of recombinant viruses in different stabilizers can be assessed.

Quantities of the modified G gene recombinant viruses such as SPBNGA-GAS-GAS can be prepared in a stirred tank bioreactor with cultures of various cells including but not limited to BHK or BSR cells. Preferably quantities of the recombinant viruses are prepared in a stirred tank bioreactor with BSR cells. Bioreactor-produced vaccine lots can be tested for their thermostability, immunogenicity, pathogenicity, and genetic stability in newborn mice.

A stirred tank reactor equipped with a fibrous bed basket on which cells grow can be used. The bioreactor can be seeded with about 10.sup.8 BHK or BSR cells suspended in MEM (MEDIATECH) supplemented with 10% fetal bovine serum, and incubated for several days at about 37° C. in batch mode. The reactor is preferably perfused with a mixture of oxygen, nitrogen, carbon dioxide at a rate to maintain the temperature, pH, and dissolved oxygen (DO) content of the medium. The composition of the gases can be monitored and controlled to maintain a pH of about 7 and a DO of about 37% throughout the incubation period.

For virus production in BSR cells, the growth medium can be removed and replaced with medium such as but not limited to OptiPro™ SFM supplemented with 4 mM glutamine and for BHK cells, growth medium can be replaced with but not limited to MEM containing 0.2% bovine serum albumin. In both cases, replacement medium contained about $10^8$ infectious virus particles. After infection, incubation temperature and pH can be decreased to about 34° C. and 6.8, respectively, and the DO maintained at about 37%, and the incubation continued for several days and up to a week or more. Killed viruses can be prepared, for example, by adding β-propiolactone to a final concentration of 0.5% BPL at neutral pH for 2 hours at 4° C.

One skilled in the art can readily determine an effective amount of nonpathogenic recombinant RVs of the invention to be administered to a given subject, by taking into account factors such as the size and weight of the subject; the extent of disease penetration; the age, health and sex of the subject; the route of administration; and whether the administration is regional or systemic. Those skilled in the art may derive appropriate dosages and schedules of administration to suit the specific circumstances and needs of the subject.

It is understood that the effective dosage will depend on the age, sex, health, and weight of the recipient, kind of concurrent treatment, if any, frequency of treatment, and the nature of the effect desired. The most preferred dosage will be tailored to the individual subject, as is understood and determinable by one of skill in the art, without undue experimentation.

The recombinant RVs of the present invention are useful for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for parenteral administration, such as intramuscular administration or administration into a body cavity or lumen of an organ. The recombinant RV compositions for administration will commonly comprise a solution of recombinant RV dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of recombinant RV in these formulations can vary widely, and will be selected primarily based on fluid volumes, viscosities, body weight and the like in accordance with the particular mode of administration selected and the subject's needs.

Thus, a typical pharmaceutical composition for intramuscular administration would be up to $10^9$ virus particles Methods for preparing parenterally administrable compositions will be known or apparent to those skilled in the art and are described in more detail in such publications as Remington's Pharmaceutical Science, 15th ed., Mack Publishing Company, Easton, Pa. (1980).

The compositions containing the recombinant RV of the present invention can be administered for therapeutic treatments. In therapeutic applications, preferred pharmaceutical compositions are administered in a dosage sufficient to block the spread of rabies virus and clear rabies virus infection. An amount adequate to accomplish this is defined as a "therapeutically effective dose." Amounts effective for this use will depend upon the severity of the disease and the general state of the subject's health.

Single or multiple administrations of the compositions may be administered depending on the dosage and frequency as required and tolerated by the subject. In any event, the composition should provide a sufficient quantity of the proteins of this invention to effectively treat the subject.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In accordance with the present invention, as described above or as discussed in the Examples below, there can be employed conventional clinical, chemical, cellular, histochemical, biochemical, molecular biology, microbiology and recombinant DNA techniques which are known to those of skill in the art. Such techniques are explained fully in the literature.

The invention should not be construed to be limited solely to the assays and methods described herein, but should be construed to include other methods and assays as well. One of skill in the art will know that other assays and methods are available to perform the procedures described herein.

EXAMPLES

Although the present invention has been described in detail with reference to examples below, it is understood that various modifications can be made without departing from the spirit of the invention, and would be readily known to the skilled artisan.

Example 1

Construction and In Vitro Characterization of the Triple G (GAS) Recombinant Rabies Virus SPBAANGAS-GAS-GAS The recombinant RVs were rescued from the cDNA clones as described (Faber et al., 2002, *J Virol* 76:3374-3381; Schnell et al., 1994, *EMBO J* 13:4195-4203), and the correct nucleotide sequences of the inserted genes were confirmed by reverse transcriptase PCR analysis and DNA sequencing.

Recombinant RV vaccine SPBNGAS is based on the prototype recombinant virus SPBN, which was derived from the SAD B19 cDNA clone (Schnell et al., 1994, *EMBO J* 13:4195-4203). The generation of the double G variant of SPBN is described elsewhere (Li et al., 2008, *Vaccine* 26:419-426; Faber et al., 2002, *J Virol* 76:3374-3381).

To facilitate insertion of a third GAS gene, AsiSI and AscI restriction sites were introduced into pSPBNGAS-GAS. A fragment between PacI and BsiWI of pSPBNGAS, containing regulatory and intergenic sequences, was amplified using Deep Vent polymerase (New England Biolabs) and primers InterG BA(+) (5'-CGA TGT ATA CGT ACG TTT TTG CGA TCG CCG TCC TTT CAA CGA TCC AAG TC-3'; SEQ ID NO:1 [BsiWI site underlined; AsiSI site in boldface]) and InterG AN(−) (5'-CTT AGC GCT AGC AAA AAG GCG CGC CGG AGG GGT GTT AGT TTT TTT CAT G-3'; SEQ ID NO:2 [NheI site underlined; AscI site in boldface]). The PCR product was digested with BsiWI and NheI and ligated into RV vaccine vector pSPBNGAS, previously digested with BsiWI and NheI, resulting in pSPBAANGAS. To insert a second copy of GAS gene, GAS cDNA was amplified with primers that contain the AscI and NheI sites: SADB19 AscI (+) (5'-CGA ATT TAT TGG CGC GCC AAGATG GTT CCT CAG GCT CTC CTG-3'; SEQ ID NO:3 [AscI site underlined; start codon in boldface]) and SADB19 NheI(−) (5'-CTT ATC AGC TAG CTA GCT AGT TAC AGT CTG GTC TCA CCC CCA-3'; SEQ ID NO:4 [NheI site underlined; stop codon in boldface]), digested with AscI and NheI, and ligated into pSPBAANGAS, previously digested with AscI and NheI resulting in pSPBAANGAS-GAS (Wiktor et al., 1984, Dev Biol Stand 57:199-211). A third copy of GAS gene was introduced in a similar manner into pSPBAANGAS-GAS (Wiktor et al., 1984, Dev Biol Stand 57:199-211) using primers: SADB19 BsiWI(+) (5'-CGA TGT ATA CGT ACG AAG ATG GTT CCT CAG GCT CTC CTG-3'; SEQ ID NO:5 [BsiWI site underlined; start codon in boldface]) and SADB19 AsiSI (−) (5'-GAA TCT AGA GCG ATC GCC GTT TAC AGT CTG GTC TCA CCC CCA-3'; SEQ ID NO:6 [AsiSI site underlined; stop codon in boldface]) resulting in pSPBAANGAS-GAS-GAS (FIG. 1). To confirm that any observations made with the triple GAS construct are due to an increased expression of G and not to the increased genome size of RV vector, pSPBAANGAS-GAS(−)-GAS(−) in which all ATG codons of the last 2 GAS genes, were scrambled (the modified gene was synthesized de novo by GenScript), was constructed.

RV vaccine strains were propagated in BSR (a BHK-21 clone) (Sato et al., 1977, *Arch Virol* 53:269-273) cells. Briefly, cells grown in DMEM (Mediatech) supplemented with 10% FBS were infected at a MOI of 0.1 and incubated for one hour at 37° C. The inoculum was then removed, and the cells were replenished with OptiPro SFM medium (Invitrogen) supplemented with 4 mM glutamine and incubated for 72 hour at 34° C. The pathogenic RV strain DOG4, which was isolated from brain tissue of a human rabies victim, was propagated in a mouse neuroblastoma (NA) cell line as described in Dietzschold et al., 2000, *J Hum Virol* 3:50-57.

Although RV variants containing 1 or 2 GAS genes have been shown to be very safe for normal animals (Faber et al., 2005, *J Virol* 79:14141-14148; Faber et al., 2007, *J Virol* 81:7041-7047), they are pathogenic for developmentally immunodeficient mice after i.c. inoculation (see FIG. 3).

Figure 2A:
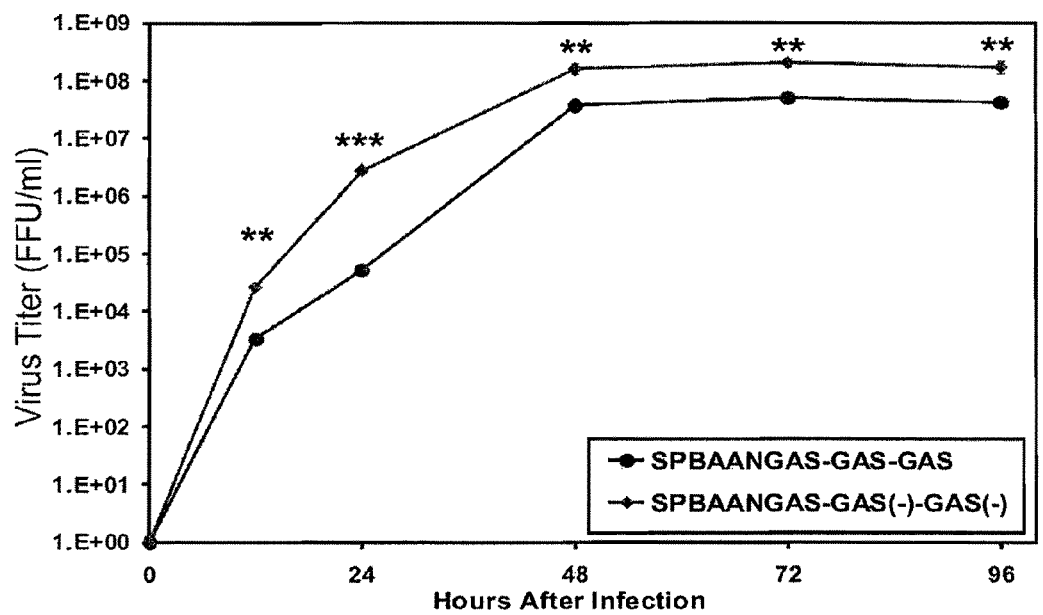
FIG. 2A is single-step growth curve for SPBAANGAS-GAS-GAS and SPBAANGAS-GAS(−)-GAS(−). Neuroblastoma (NA) cells were infected in duplicate at a multiplicity of infection (MOI) of 5, and the titers of virus in the tissue culture supernatants were determined at the indicated time points. Data are the means (±SE) of results from 3 independent experiments. *, $P<0.05$; , $P<0.01$; *, $P<0.001$).

The effect of triplication of the GAS gene on virus production was analyzed in the NA cell line with a single-step growth curve being examined (FIG. 2A). In the single-step growth kinetics, the replication rate of SPBAANGAS-GAS-GAS was significantly lower between 12 and 24 hour post infection (p.i.) than that of SPBAANGAS-GAS(−)-GAS(−) ($\approx$1 log; $P<0.001$). However, after 24 h p.i., the growth rate of SPBAANGAS-GAS-GAS increased substantially and approximated that of SPBAANGAS-GAS(−)-GAS(−).

Figures 2B, 2C:
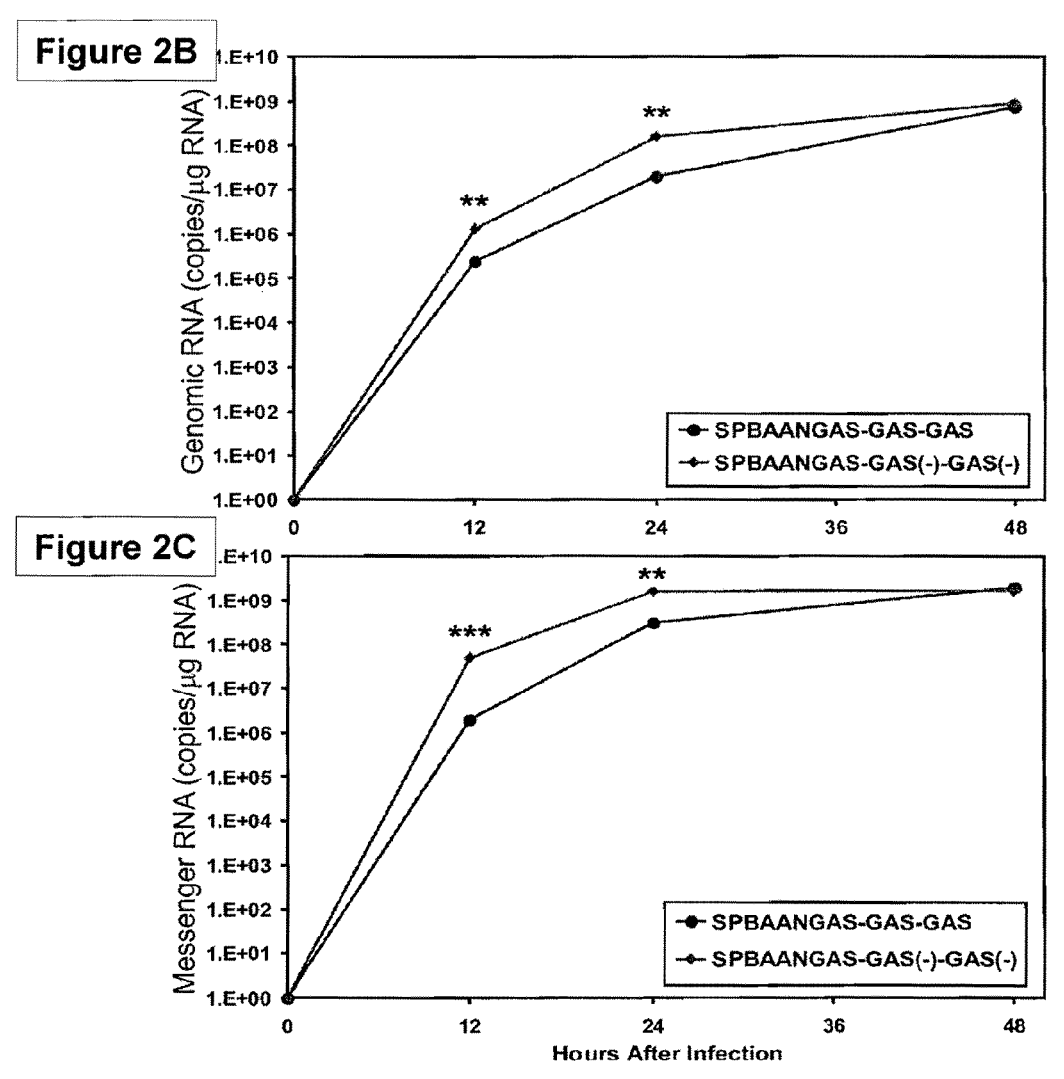

The retardation in virus production during the early phase of SPBAANGAS-GAS-GAS infection was paralleled by a reduced rate of viral RNA synthesis. qRT-PCR analysis at 12 and 24 hour p.i. detected significantly less viral genomic and messenger RNA in SPBAANGAS-GAS-GAS- than in SPBAANGAS-GAS(−)-GAS(−)-infected NA cells whereas at 48 h p.i., the amounts of viral RNA were similar for both viruses (FIGS. 2B and 2C). Fluorescence-activated "cell sorter" analysis of the surface expression of RV G was used to determine whether the differences in viral RNA synthesis rates were reflected in the levels of G protein expression and revealed higher levels of surface expression of G in SPBAANGAS-GAS(−)-GAS(−)-infected than in SPBAAN-GAS-GAS-GAS-infected cells at 12 h and, in particular, at 24 h p.i. However, at 48 h p.i., the G expression levels were identical for both viruses.

Example 2

The Triple GAS RV Variant has Limited Pathogenicity in Suckling Mice

To examine whether the presence of 3 GAS genes further decreases the pathogenicity in young mice of RV vaccine candidates, groups of 8-15 one-, five-, and ten-day-old Swiss-Webster mice were inoculated intracranial/intracerebrally (i.c.) with $10^3$ focus-forming units (FFU) of SPBNGAS, SPBNGAS-GAS, SPBAANGAS-GAS-GAS, or SPBAAN-GAS-GAS(−)-GAS(−) (in 5 µl PBS) and observed for occurrence of clinical signs of rabies.

Figure 3:
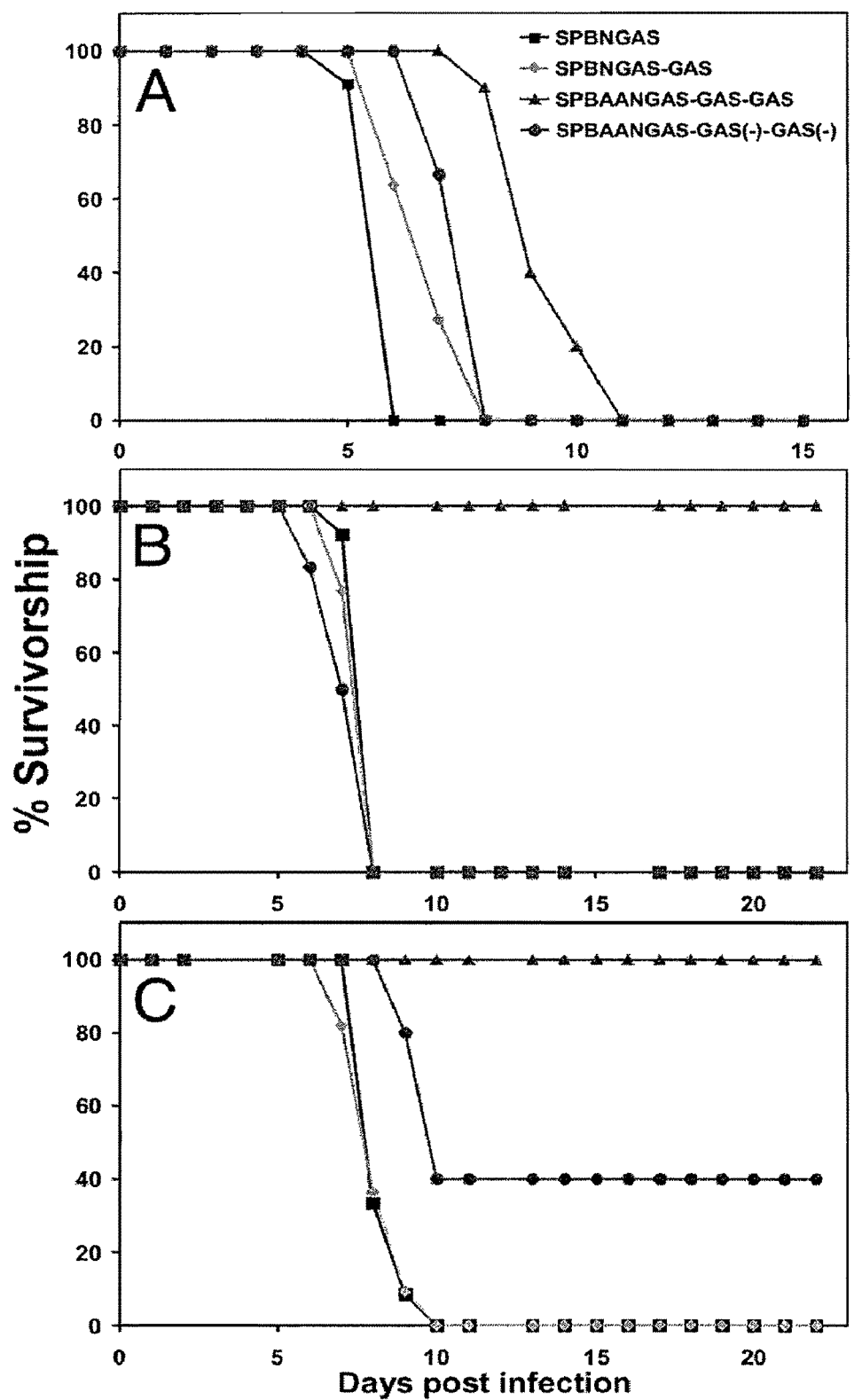
FIG. 3, comprising

Although all 1-, 5-, or 10-day-old mice inoculated i.c. with SPBNGAS or SPBNGAS-GAS succumbed to infection between 6 and 10 days afterward, all five- and ten-day-old mice infected i.c. with SPBAANGAS-GAS-GAS did not develop any clinical signs of infection and survived (FIG. 3). Moreover, although all one-day-old mice infected with SPBAANGAS-GAS-GAS died, they died much later than SPBNGAS or SPBNGAS-GAS-infected one-day-old mice (8-11 days after infection). Notably, 100% and 60% of the five- and ten-day-old mice infected with SPBAANGAS-GAS (−)-GAS(−) succumbed (FIG. 3), indicating that although the increase in the genome size may somewhat contribute to the attenuation of SPBAANGAS-GAS-GAS, the strong reduction of its pathogenicity is primarily because of increased G expression.

Example 3

Immunogenicity of SPBAANGAS-GAS-GAS in Young and Adult Mice

In order to assess immunogenicity of triple GAS, mice were injected i.c. with $10^3$ FFU of SPBNGAS, SPBNGAS-GAS, SPBAANGAS-GAS-GAS or SPBAANGAS-GAS(−)-GAS(−) in 5 µL PBS. One litter of 8-15 mice was used for each virus. Twenty-one days after infection, blood samples were obtained from the surviving mice and viral neutralizing antibody (VNA) titers were determined by using the rapid fluorescence inhibition test. Six 8-week-old Swiss-Webster or various mutant mice were infected i.c. under anesthesia with 5 µL PBS containing $10^7$ FFU SPBNAAGAS-GAS-GAS, 100 50% i.c. lethal doses (IC-LD$_{50}$) of DOG4 RV, or a mixture of $10^7$ FFU of SPBNAAGAS-GAS-GAS and 100 IC-LD$_{50}$ of DOG4 RV. Intramuscular (i.m.) infection of adult Swiss-Webster mice was performed under anesthesia by injecting PBS containing 10 50% i.m. lethal doses (IM-LD$_{50}$) of DOG4 RV into the gastrocnemius (100 µL) or masseter (50 µL) muscles. After infection, mice were observed for 30 days for clinical signs of rabies and mortality rates were recorded daily.

It was observed that mice infected i.c. at day 5 or day 10 after birth produced high virus neutralizing antibody (VNA) titers by 21 days after infection (24 and 41 IU, respectively) and were completely protected against an i.c. challenge infection with DOG4 RV.

Figure 4:
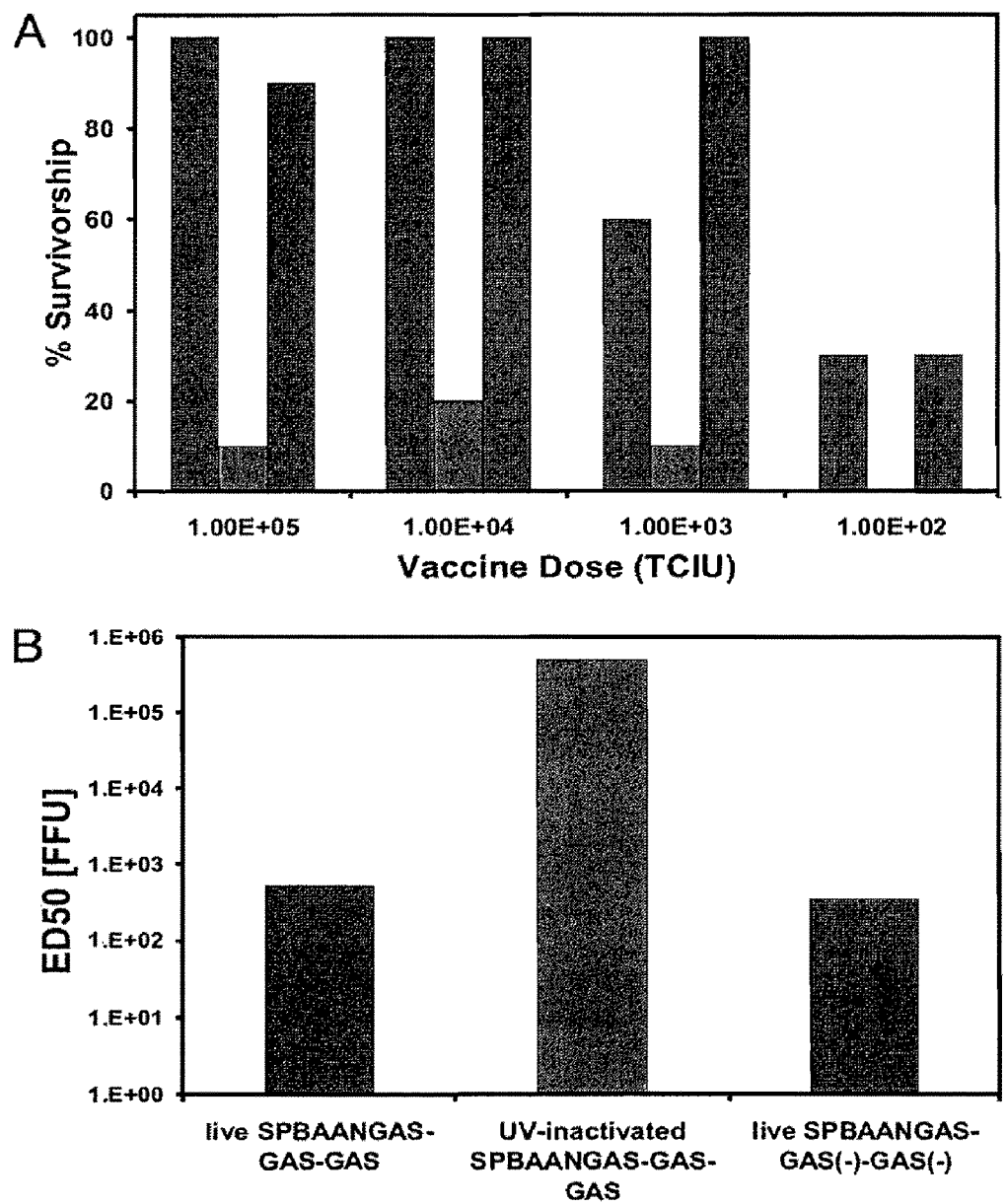
FIG. 4, comprising

These results demonstrate that, despite its decreased pathogenicity for suckling mice, SPBAANGAS-GAS-GAS is also highly immunogenic for very young mice. Adult mice that were immunized i.m. with a single dose containing $10^5$ or $10^4$ FFU of SPBAANGAS-GAS-GAS were completely protected against an i.c. challenge infection with DOG4 RV that killed 100% of the mock-immunized mice (FIG. 4). Notably, the $ED_{50}$ of SPBAANGAS-GAS-GAS was similar to that of SPBAANGAS-GAS(−)-GAS(−) (FIG. 4). However, UV inactivation of SPBAANGAS-GAS-GAS resulted in a >1,000-fold increase in the $ED_{50}$.

Example 4

Effect of SPBNAAGAS-GAS-GAS on the Outcome of an i.c. Infection with DOG4 RV in Normal and Immunodeficient Mice To examine whether i.c. administration of SPBNAAGAS-GAS-GAS can prevent lethal CNS infection with RV, groups of 10 six- to eight-week-old BALB/c or C57BL/6 mice were infected i.c. with $10^6$ FFU of SPBNAAGAS-GAS-GAS, 100 50% effective doses (IC-$LD_{50}$) of the highly pathogenic DOG4 RV, or a mixture of $10^7$ FFU of SPBAANGAS-GAS-GAS and 100 IC-$LD_{50}$ of DOG4 RV. Although i.c. infection with DOG4 RV alone caused 100% and 90% mortality in BALB/c or C57BL/6 mice, respectively, no mortality was seen in these mice after infection with a mixture of DOG4 RV and SPBAANGAS-GAS-GAS (Table 1).

TABLE 1

Mortality after i.c. infection of wild-type and mutant mice with SPBAANGAS-GAS-GAS (Tri GAS), DOG4 RV, or a mixture of SPBAANGAS-GAS-GAS and DOG4 RV

| Mouse strain | Mortality after i.c. virus infection | | |
|---|---|---|---|
| | Tri GAS | DOG4 RV | Tri GAS + DOG4 RV |
| Balb/C | ND | 9/9 | 0/10 |
| C57BL/6 | ND | 9/10 | 0/10 |
| B6-129-μMT−/− | 0/9 | ND | 5/5 |
| C57BL/6- MyD88−/− | 0/5 | ND | 7/7 |
| BALB/c- IFN-α/β R−/− | 0/6 | 10/10 | 11/11 |

The next set of experimens was designed to assess the nature of the immune effectors induced by SPBAANGAS-GAS-GAS that play a role in preventing a lethal i.c. infection with DOG4 RV. Mice lacking B cells (μMT−/−), or that had a defective TLR and IL-1 receptor signaling pathway (MyD88−/−), or were deficient in type I IFN responses (IFN-α/β R−/−) were coinfected i.c. with DOG4 RV and SPBAAN-GAS-GAS-GAS. As shown in Table 1, 100% of the μMT−/−, and IFN-α/β R−/− mice succumbed to the infection with the DOG4/SPBAANGAS-GAS-GAS mixture. These data suggest that the antibody production and innate immune response are both important in preventing a lethal infection with DOG4 RV.

Example 5

Effect of SPBAANGAS-GAS-GAS on Immune Effector Delivery to CNS Tissues

The capacity to induce the mechanisms that deliver rabies-specific immune effectors into CNS tissues is an important feature that differentiates effective vaccine variants from pathogenic rabies viruses (Roy et al., 2008, *J Neurovirol* 14:401-411). Elevated blood-brain barrier (BBB) permeability to fluid phase markers, which generally occurs between 6 and 12 days after immunization (Phares et al., 2006, *J Immunol* 176:7666-7675), is a reflection of this process. Consequently, BBB permeability to sodium fluorescein (NaF) was assessed in brain tissues from adult C57BL/6 mice infected i.c. with SPBAANGAS-GAS-GAS in the right cerebral cortex 6 and 8 days previously as discussed below.

Fluid phase BBB permeability was assessed as described in Hooper et al., 2000, *FASEB J* 14:691-698. Briefly, mice received 100 μL of 10% sodium fluorescein (NaF, 376 molecular weight, Sigma) in PBS i.p. and 10 minute later were anesthetized, bled, and transcardially perfused with PBS/heparin (1,000 units per liter) and PBS. Brains were removed and separated into left and right cerebral cortex hemispheres and cerebellum. Brains tissues were homogenized in PBS, centrifuged, and the fluorescent marker content in the clarified supernatant determined in a Cytofluor II fluorimeter (PerSeptive Biosystems). Specific NaF content was calculated with the use of standards and uptake from the circulation into CNS tissue is expressed as (μg fluorescence CNS tissue/mg protein)/(μg fluorescence sera/μL blood) to normalize values for blood levels of the marker. The results are expressed as the level of fluorescein in the tissues with the levels detected in tissues from similarly treated normal mice taken as 1.

Figure 5:
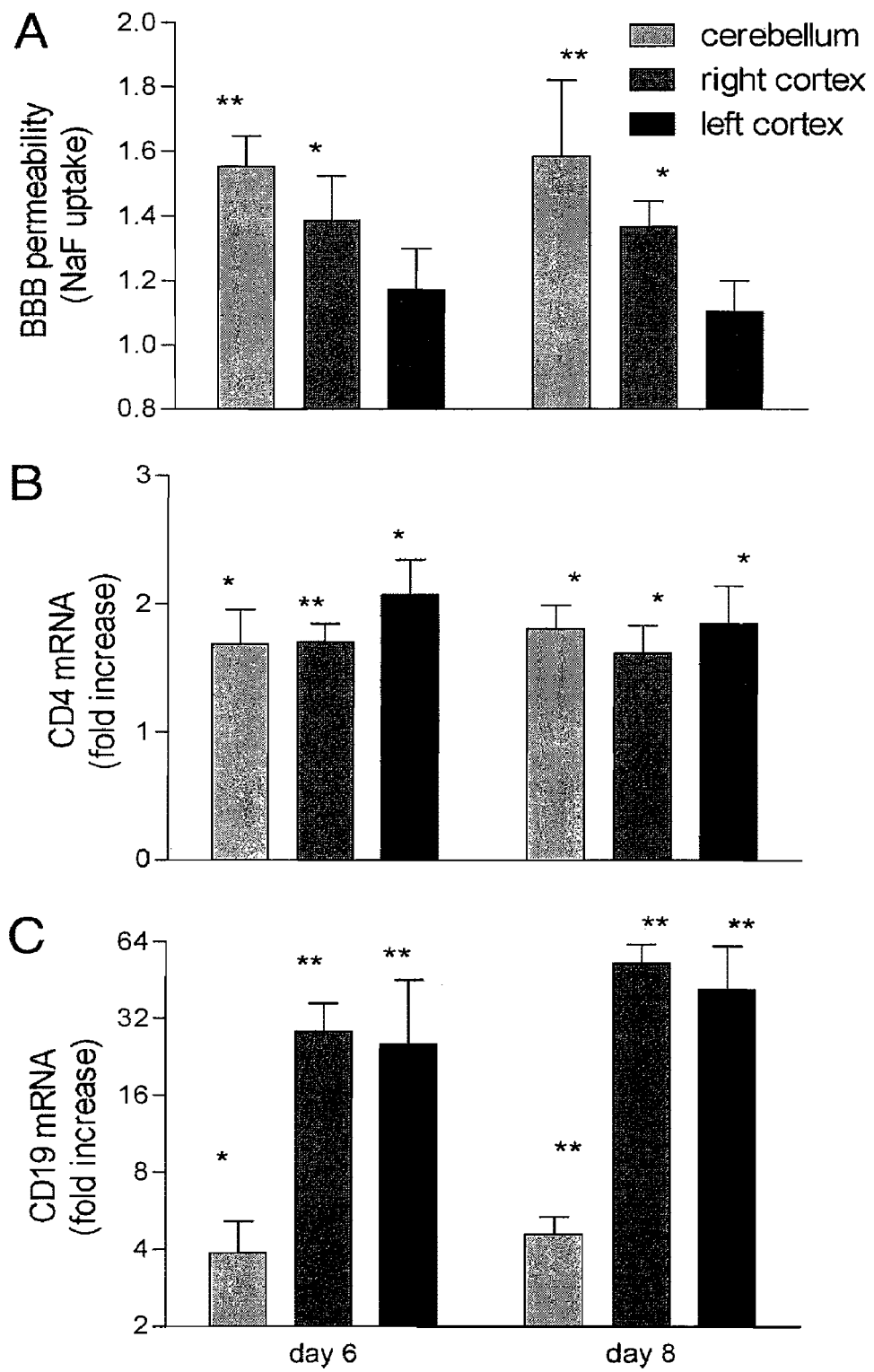
FIG. 5, comprising

As shown in FIG. 5A, BBB permeability to NaF is significantly elevated in the right cortex and cerebellum. Elevated expression of CD4 (FIG. 5B) and CD19 (FIG. 5A) was also detected. CD19 was detected primarily in the cortex. CD19 mRNA levels were particularly elevated, appearing at high levels in both cortical hemispheres within 6 days of infection. It is believed that immune cells are being delivered into the CNS tissues with a bias in B cell accumulation in the tissues where virus replication is most likely.

Example 6

Postexposure Efficacy of SPBAANGAS-GAS-GAS

The next set of experiments was designed to test whether treatment with the SPBAANGAS-GAS-GAS vaccine can prevent a lethal street RV infection.

For preexposure immunization against rabies, groups of ten 6- to 8-week-old female Swiss-Webster mice were inoculated i.m. with 100 μL of serial 10-fold dilutions of live recombinant RV. After 14 days, the animals were injected i.c. under isoflurane anesthesia with 5 μL containing 100 IC-$LD_{50}$ of DOG4 RV. To determine the postexposure efficacy of SPBAANGAS-GAS-GAS, groups of 10 6- to 8-week-old female Swiss-Webster mice were infected i.m. (gastrocnemius muscle) with 100 μL PBS containing 10 IM-$LD_{50}$ of DOG4 RV. At different times after infection ranging from 4 hour to 5 days, the mice were treated either i.c. with 5 μL containing $10^7$ FFU of SPBAANGAS-GAS-GAS or i.m. (masseter muscle) with 50 μL containing $10^8$ FFU of SPB-NAAGAS-GAS-GAS. A control group of ten mice received 5 μL PBS i.c. and two other control groups of ten mice were treated i.m. with 100 μL PBS or with 100 μL UV-inactivated SPBAANGAS-GAS-GAS. After virus challenge, mice were observed for 4 weeks for clinical signs of rabies. Mice that showed definitive clinical signs of rabies such as paralysis, tremors, and spasms were euthanized by $CO_2$ intoxication.

Although 100% of the mice treated with PBS developed severe rabies encephalomyelitis and succumbed to the infection, none of the mice that were treated 4 hours after infection with live SPBAANGAS-GAS-GAS died (FIG. 6A) or developed clinical signs of rabies. All mice that were treated i.c. 48 h p.i. with live SPBAANGAS-GAS-GAS developed hind limb paralysis, but none of these mice died, and 60% recovered fully between 16 and 21 days p.i. Even when i.c. immunization was initiated as late as 4 days after street RV challenge, 50% of the animals survived.

Figure 6:
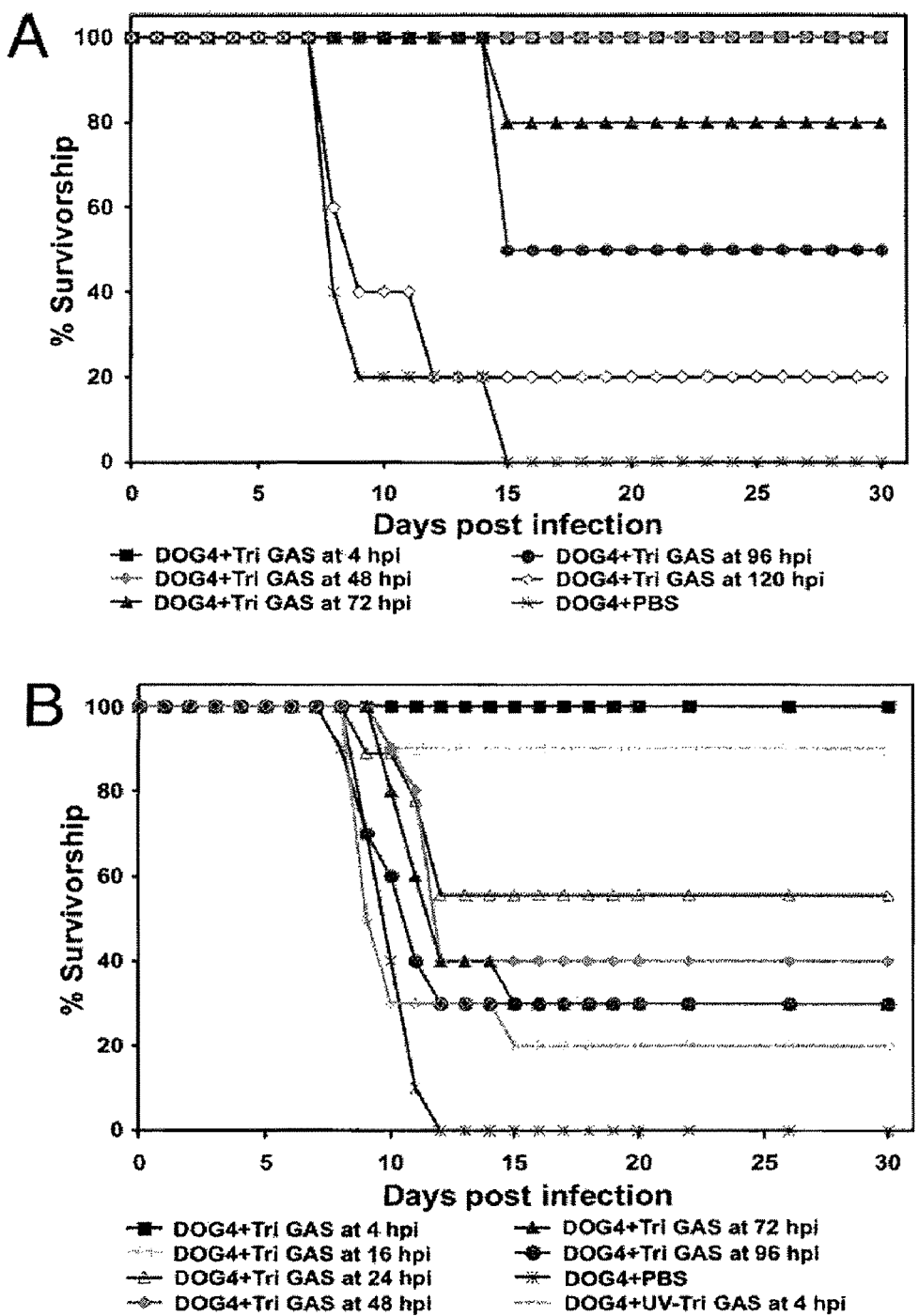
FIG. 6, comprising

The next set of experiments was designed to investigate whether the SPBAANGAS-GAS-GAS vaccine is also efficacious when administered by the i.m. route after an i.m. infection with $10^6$ FFU of DOG4 RV. FIG. 6B shows that no mortality was seen when $10^8$ FFU of live SPBAANGAS-GAS-GAS were injected into the masseter muscle at 4 hour after infection with DOG4 RV. Notably, i.m. treatment with UV-inactivated SPBAANGAS-GAS-GAS at 4 hours after infection protected only 20% of the mice, indicating that the protective activity of SPBAANGAS-GAS-GAS against a lethal RV infection of the CNS depends largely on the capacity of the vaccine virus to replicate. When i.m. treatment with SPBAANGAS-GAS-GAS was performed at 16, 24, 48, and 72 hours after virus challenge, 90%, 55%, 40%, and 30% of the mice, respectively, survived. Although no clinical signs were seen in animals treated at 4 h p.i., between 50% and 90% of the mice treated i.m. at the later time points developed hind limb paralysis. Because i.c. or i.m. treatment of uninfected mice with SPBAANGAS-GAS-GAS does not cause any clinical signs, it is believed that the pathogenic RV infection had already damaged spinal cord neurons before the virus was cleared.

Example 7

Effective Preexposure and Postexposure Prophylaxis of Rabies with a Highly Attenuated Recombinant Rabies Virus The results presented herein demonstrate a successful rabies vaccine that safe and able to confer long-lasting immunity after a single administration.

In order to test the safety of SPBAANGAS-GAS-GAS, pathogenicity for suckling mice was assessed because these mice are not fully immunocompetent until approximately 6 weeks of life. The results revealed that the pathogenicity of the triple GAS RV is considerably lower for suckling mice than that of the single and double GAS recombinant RV. The pathogenicity of the triple GAS variant is also significantly lower than that of a recombinant RV in which 2 of the 3 G genes are inactive [SPBAANGAS-GAS(−)-GAS(−)]. This strongly suggests that the higher level of attenuation of SPBAANGAS-GAS-GAS is primarily because of increased G expression rather than an increase in the size of the genome. Somewhat paradoxically, SPBAANGAS-GAS-GAS-infected cells initially express lower levels of G than SPBAAN-GAS-GAS(−)-GAS(−)-infected cells. It is believed that the reason for this phenomenon is that the over-expression of the G in SPBAANGAS-GAS-GAS-infected cells after primary RNA transcription, which is undetectable using available technology, results in a cellular stress response that causes the transient inhibition of virus replication (Medigeshi et al., 2007, *J Virol* 81:10849-10860). Despite a brief lag period in G production, the triple GAS RV variant rapidly begins to produce high levels of G protein and is highly immunogenic. It is noteworthy in this regard that 5- and 10-day-old mice infected i.c. with SPBAANGAS-GAS-GAS exhibit high levels of VNA at day 21 p.i. and are fully protected against a subsequent i.c. RV challenge infection that kills 100% of unvaccinated control mice. This finding implies that a triple GAS vaccine is safe and effective for young dogs and present little risk for young children who may be exposed to the virus.

An important factor in controlling and eventually eradicating dog and dog-associated human rabies worldwide is the availability of a potent but affordable vaccine. Because of the ability to replicate, thereby producing relatively large amounts of antigen from a small input dose, a live-attenuated vaccine would be expected to be considerably less expensive than a killed RV vaccine product. In addition, the requirement for multiple boost doses of vaccine would be reduced. Immunization with a single dose of triple GAS vaccine containing as little as $5 \times 10^2$ live virus particles protects 50% of mice ($ED_{50}$) against a lethal RV infection after with complete protection being achieved when $10^4$ virus particles are administered. In contrast, the $ED_{50}$ of UV-inactivated SPBAAN-GAS-GAS-GAS is >1,000 times higher than that of the live virus. This indicates that the high efficacy of the triple GAS variant depends on its ability to replicate in addition to providing insight into how much more costly a killed vaccine would be.

The postexposure treatment experiments with mice discussed elsewhere herein demonstrate that lethal rabies encephalopathy can be prevented by administering live but not UV-inactivated SPBAANGAS-GAS-GAS up to several days after infection with a highly pathogenic wildlife RV strain. This suggests that the live triple GAS vaccine can also be effective for delayed rabies PEP in humans. In contrast to mice, in which disease development rapidly occurs after street virus infection (5 to 6 days p.i.) and is lethal within 2 or 3 days after the onset of clinical signs, the average incubation time of rabies in humans varies between 1 and 2 months. In addition, the disease can last several weeks from the onset of the prodromal period to the development of acute neurological disease, the progression to coma, and death. This is more than sufficient time for SPBAANGAS-GAS-GAS to induce a RV-clearing immune response, particularly because it promotes immune effector entry into infected CNS tissues.

The mechanism by which postexposure treatment with SPBAANGAS-GAS-GAS prevents a lethal encephalopathy is not exactly known. The observation that immunocompetent mice, but not mice that are deficient in B cells or have defective type I IFN, TLR, or IL-1 receptor signaling pathways, survived an i.c. infection with a mixture of DOG4 RV and SPBAANGAS-GAS-GAS strongly suggests that adaptive immune responses as well as innate immune responses are required to clear the RV from the brain. It is believed that there are 2 characteristics of SPBNAAGAS-GAS-GAS that enable it to rapidly induce an immune response capable of clearing pathogenic RV: 1) enhanced stimulation of antiviral and proinflammatory mechanisms through the NFκB signaling pathway; and 2) overcoming the failure of pathogenic RV to trigger BBB permeability changes and the delivery of immune effectors to the CNS. In addition to the induction of innate and adaptive immune responses, the delivery of immune effectors across the BBB is necessary for clearance of RV from the CNS. Infection with attenuated but not with pathogenic RVs triggers BBB permeability changes and the invasion of immune effectors into CNS tissues (Roy et al., 2008, *J Neurovirol* 14:401-411; Roy et al., 2007, *J Virol* 81:1110-1118). SPBAANGAS-GAS-GAS effectively induces BBB permeability and the delivery of immune cells into CNS tissues.

The use of the highly attenuated triple GAS vaccine, which is able to induce protective immunity after a single immunization, could make global eradication of canine rabies more feasible. In addition, because of its ability to prevent the fatal outcome of the disease by overcoming immune evasion of pathogenic RVs, this vaccine may have utility for human PEP, particularly in situations where the RV has already reached the CNS tissues and current PEP regimens fail.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A nonpathogenic recombinant rabies virus comprising at least three copies of a mutated G gene, wherein said mutated G gene encodes a rabies virus glycoprotein wherein the amino acid 194 is serine and the amino acid 333 is glutamic acid in the glycoprotein.

2. The recombinant rabies virus of claim 1, wherein said mutated G gene is encoded by SEQ ID NO:7.

3. The recombinant rabies virus of claim 1 further comprising a foreign antigen.

4. The recombinant rabies virus of claim 3 wherein said antigen is derived from a human or an animal pathogen.

5. The recombinant rabies virus of claim 1 further expressing a gene encoding an immune-stimulatory protein.

6. A vaccine comprising the recombinant rabies virus of claim 1.

7. A pharmaceutical composition comprising the recombinant rabies virus of claim 1, and a pharmaceutically acceptable carrier.

8. A method of inducing an immune response to rabies virus in a mammal, comprising administering to said mammal an effective amount of a nonpathogenic recombinant rabies virus comprising at least three copies of a mutated G gene, wherein said mutated G gene encodes a rabies virus glycoprotein wherein the amino acid 194 is serine and the amino acid 333 is glutamic acid in the glycoprotein.

9. A method of protecting a mammal from rabies virus, comprising administering to said mammal an effective amount of a nonpathogenic recombinant rabies virus comprising at least three copies of a mutated G gene, wherein said mutated G gene encodes a rabies virus glycoprotein wherein the amino acid 194 is serine and the amino acid 333 is glutamic acid in the glycoprotein.

* * * * *